United States Patent
Dollinger et al.

(10) Patent No.: US 10,441,817 B2
(45) Date of Patent: Oct. 15, 2019

(54) METHOD AND APPARATUS FOR DETERMINING AN ENERGY DEPOSITION OF AN ION BEAM

(71) Applicants: Ludwig-Maximilians-Universität München, München (DE); Universität der Bundeswehr München, Neubiberg (DE)

(72) Inventors: Günther Dollinger, Garching (DE); Katia Parodi, München (DE); Walter Assmann, München (DE); Vasilis Ntziachristos, Gräfelfing (DE); Stephan Kellnberger, Künzing (DE)

(73) Assignees: Ludwig-Maximilians-Universität München, München (DE); Universität der Bundeswehr München, Neubiberg (DE)

( * ) Notice: Subject to any disclaimer, the term of this patent is extended or adjusted under 35 U.S.C. 154(b) by 437 days.

(21) Appl. No.: 15/327,056

(22) PCT Filed: Jul. 17, 2015

(86) PCT No.: PCT/EP2015/066412
§ 371 (c)(1),
(2) Date: Jan. 18, 2017

(87) PCT Pub. No.: WO2016/009042
PCT Pub. Date: Jan. 21, 2016

(65) Prior Publication Data
US 2017/0165504 A1    Jun. 15, 2017

(30) Foreign Application Priority Data

Jul. 18, 2014 (EP) .................................... 14177712
Aug. 27, 2014 (EP) .................................... 14182487

(51) Int. Cl.
*A61N 5/10* (2006.01)

(52) U.S. Cl.
CPC ......... *A61N 5/1049* (2013.01); *A61N 5/1048* (2013.01); *A61N 2005/1058* (2013.01);
(Continued)

(58) Field of Classification Search
CPC .......... A61N 2005/1058; A61N 5/1049; A61N 5/1048; A61N 2005/1095; A61N 2005/1087; A61N 2005/1088
See application file for complete search history.

(56) References Cited

FOREIGN PATENT DOCUMENTS

| WO | WO 2011/100753 | 8/2011 |
| WO | WO 2013/134782 | 9/2013 |

OTHER PUBLICATIONS

Tada et al., "Time resolved properties of acoustic pulses generated in water and in soft tissue by pulsed proton beam irradiation—A possibility of doses distribution monitoring in proton radiation therapy." *Medical physics* 18.6 (1991): 1100-1104.
(Continued)

*Primary Examiner* — Michael W Kahelin
(74) *Attorney, Agent, or Firm* — Sunstein Kann Murphy & Timbers LLP (57) ABSTRACT

Disclosed is a method of determining information regarding the location of energy deposition of an ion beam, in particular a proton beam, in an absorptive medium, in particular in the tissue of a patient undergoing radiation therapy, comprising the following steps:
  generating an intensity modulated ion beam, wherein the intensity modulation comprises one or more modulation frequency components,
  detecting an acoustic signal attributable to the time dependent energy deposition in said absorptive medium by said intensity modulated ion beam using at least one detection apparatus, said detection apparatus being preferably configured for extracting at least one modu- (Continued)

lation frequency component of the acoustic signal corresponding to a respective one of the one or more modulation frequency components of said intensity modulation, or a harmonic thereof, and deriving information regarding the location of the energy deposition based, at least in part, on a time lag between the timing of the intensity modulation of said ion beam and said acoustic signal.

25 Claims, 7 Drawing Sheets

(52) U.S. Cl.
CPC ................ *A61N 2005/1087* (2013.01); *A61N 2005/1088* (2013.01); *A61N 2005/1095* (2013.01)

(56) References Cited

OTHER PUBLICATIONS

International Searching Authority—European Patent Office, International Search Report and Written Opinion, PCT/EP2015/066412, dated Oct. 7, 2015; 12 pages.

METHOD AND APPARATUS FOR DETERMINING AN ENERGY DEPOSITION OF AN ION BEAM

FIELD OF THE INVENTION

While not strictly limited to medical sciences, the present invention finds particular use in the field of radiation therapy. More precisely, the invention relates to a method and an apparatus for determining information regarding the location of energy deposition of an ion beam, in particular a proton beam, in an absorptive medium, such as in the tissue of a patient undergoing radiation therapy.

BACKGROUND OF THE INVENTION

In radiation therapy, ionizing radiation is used for medical purposes, in particular as part of cancer treatment to control or kill malignant cells. The most common type of radiation therapy is based on x-ray photons. MeV photons can be generated with moderate effort using for example a linear accelerator for accelerating an electron beam that is directed to a target to generate x-ray radiation as Bremsstrahlung. However, in x-ray radiation therapy, one always has to cope with the problem that the dose cannot be confined to the tumor area, but also affects healthy tissue. Part of this problem is due to the fact that the energy deposition of an x-ray beam in human tissue decreases nearly exponentially along the penetration depth and that the x-ray radiation will also affect healthy tissue in front of and behind the target area, since the x-rays are typically applied from outside.

Figure 1:
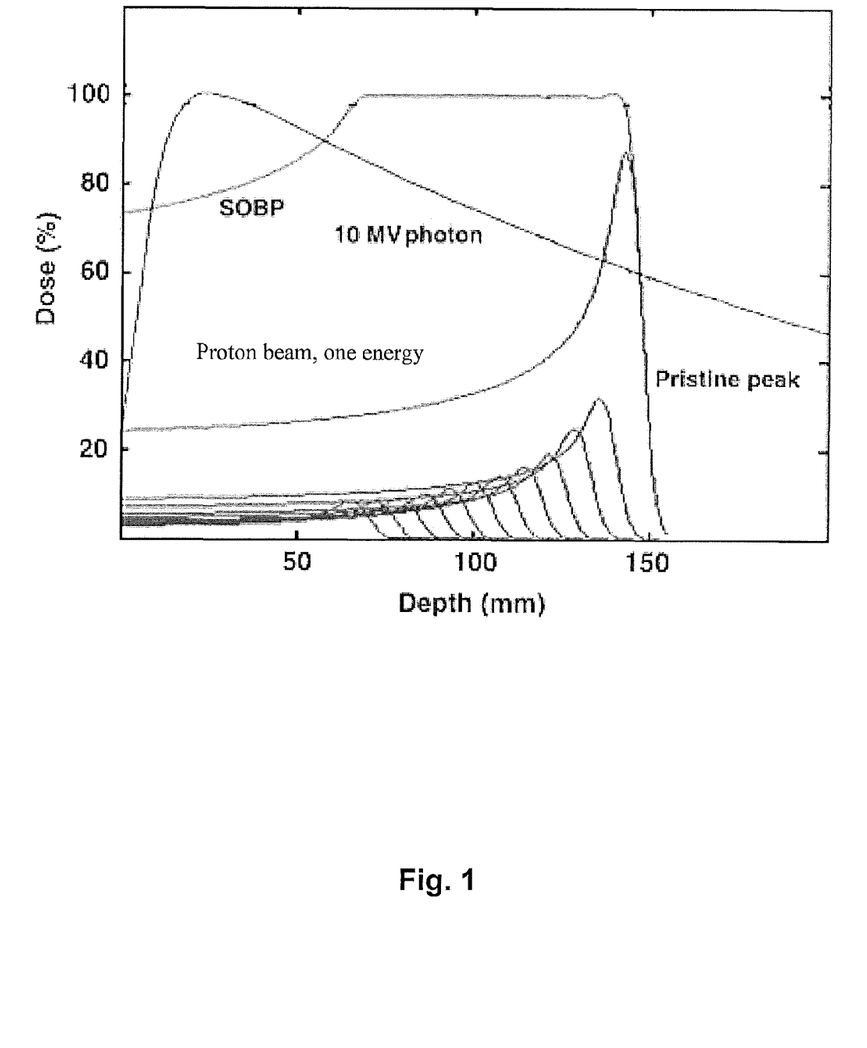
FIG. 1 is a diagram showing the dose vs. penetration depth of a 10 MeV photon and a plurality of proton beams of different energies.

In contrast to this, using charged particles, such as protons, boron ions, carbon ions or neon ions, the damage to healthy tissue can be significantly reduced. To appreciate this, reference is made to FIG. 1, where the energy deposition or dose of a 10 MeV photon as a function of penetration depth is compared with that of several proton beams of different energies. As is seen in FIG. 1, the so-called Bragg curve of the energy loss versus penetration depth shows a pronounced peak immediately before the protons come to rest. In the art these peaks are referred to as "Bragg peaks". The penetration depth or location of the Bragg peak depends on the energy of the proton beam: The higher the energy, the larger the penetration depth. By combining a plurality of proton beams with different energies, a dose as shown by the envelope curve in FIG. 1 can be obtained, which has a maximum in a certain target region, which is below this maximum between the ion source and the target region and which drops sharply to zero behind the target region. Accordingly, using protons or other ions in radiation therapy, an adverse effect to healthy tissue in front of and behind the tumor region can be drastically reduced as compared to x-ray radiation.

While ion radiation therapy therefore has the capability of a more precise targeting of the tumor as compared to x-ray radiation therapy, the beneficial effect clearly depends on whether one is able to precisely deliver the dose to the target region as planned. This in fact remains one of the current challenges of ion radiation therapy. In particular, it is currently not possible to predict the precise location of the Bragg peak along the ion beam axis with a desired precision, which precision needs to be particularly high if organs at risk are located just behind the target region. Accordingly, there is a need to monitor the actual dose delivered during the therapeutic irradiation ("in vivo").

Among the recent attempts to measure the dose in vivo are those related to secondary radiation employing, e.g. positron emission tomography (PET) and gamma imaging, see for example Ben Mijnheer et al., "*In vivo dosimetry in external beam radiotherapy*", Med. Phys. 40 (7), July 2013 and Antje-Christin Knopf and Antony Lomax, "*In vivo proton range verification: a review*", Phys. Med. Biol. 58 (2013) R131-R160.

However, these recent methods rely on complex instrumentation, and they do not allow for a straightforward correlation between the secondary radiation and the real dose distribution, so that a Bragg peak positioning accuracy better than a few millimeters cannot be expected in clinical situations.

In J Tada et al., "*Time Resolved Properties of Acoustic Pulses Generated in Water and in Soft Tissue by a Pulsed Proton Beam Irradiation—A Possibility of Dose Distribution Monitoning in Proton Radiation Therapy*", Med. Phys. 18 (6), 1991, time-resolved acoustic pulses were generated in water and soft tissue by pulsed proton beam irradiation. The spatial resolution of depth dose distribution at the clinically applied beam intensity using time-of-flight measurement was estimated to be about 3 mm. In following experiments by the same research group, acoustic pulse signals have been observed even during therapy, see Y. Hayakawa et al., "*Acoustic Pulse Generated in a Patient During Treatment by Pulsed Proton Radiation Beam, Radiation Oncology Investigations*", 3 (1995), 42-45.

However, while this method for monitoring dose distribution has been proposed more than 20 years ago, it has so far not led to any practical applications.

SUMMARY OF THE INVENTION

It is a problem underlying the invention to provide a method and an apparatus for determining information regarding the location of energy deposition of an ion beam, in particular a proton beam, in an absorptive medium, such as in the tissue of a patient undergoing radiation therapy.

The method of the invention comprises a step of generating an intensity modulated ion beam, wherein the intensity modulation comprises one or more modulation frequency components. The method further comprises a step of detecting an acoustic signal attributable to the time dependent energy deposition in said absorptive medium by said intensity modulated ion beam using at least one detection apparatus. Herein, said detection apparatus is preferably configured for extracting at least one modulation frequency component of the acoustic signal corresponding to a respective one of the one or more modulation frequency components of said intensity modulation, or a harmonic thereof. Finally, the method comprises a step of deriving information regarding the location of the energy deposition based, at least in part, on a time lag between the timing of the intensity modulation of said ion beam and said acoustic signal.

Similar to the aforementioned works of Tada et al. and Hayakawa et al., the method of the invention is based on acoustic signals generated by the ion/proton beam. Simply speaking, such acoustic signals are due to thermal shockwaves caused by the instantaneous heat deposited by the incident ions/protons. However, unlike the methods of Tada et al. and Hayakawa et al., the method of the invention is not based on individual independent pulses and time-of-flight measurements only. Instead, according to the invention, the intensity of the ion beam is modulated, wherein the intensity modulation comprises one or more modulation frequency components. It is seen that with such a modulation or "frequency information", the method can be dramatically improved as compared to methods based on individual pulses and simple time-of-flight measurements only.

Using an ion beam that is modulated with one or more predetermined frequencies will lead to acoustic signals that likewise carry the frequency information. This has several important advantages. One advantage is that since the acoustic signals will exhibit the same frequency as the intensity modulation of the ion beam; this frequency information can be used for filtering out the signals from the background. Accordingly, in a preferred embodiment, the detection apparatus can be adapted to extract at least one modulation frequency component of the acoustic signal corresponding to a respective one of the one or more modulation frequency components of the intensity modulation, for example by using a narrowband filter or a lock-in amplifier. This way the acoustic signals, which typically will be comparatively weak, can be better distinguished from the background.

However, the invention is not limited to this, and the frequency information can be used for other purposes, and in particular for a more sophisticated reconstruction of the dose distribution as well. For example, it is possible to determine higher moments of the energy deposition based on an analysis of higher harmonics of the modulation frequency components in the detected acoustic signals. Finally, using an ion beam with an intensity modulation of known frequency or frequencies, an improved time resolution in the determination of a time lag and hence an improved spatial resolution of the energy deposition can be obtained.

Preferably, the time lag is determined by determining a relative phase between the intensity modulation of the ion beam and the acoustic signal.

In a preferred embodiment, the intensity modulation comprises one or more modulation frequency components in a range of 1 kHz to 10 MHz, preferably in a range of 10 kHz to 3 MHz. It is seen that modulation frequency components in this range will lead to acoustic signals that allow for a good detection.

In a preferred embodiment, the intensity modulation comprises a higher modulation frequency component and a lower modulation frequency component, wherein the frequency of the higher modulation frequency component exceeds the frequency of the lower modulation frequency component by a factor of at least 2, preferably by a factor of at least 5, and most preferably by a factor of at least 10. In many applications, a higher modulation frequency component leads to acoustic signals that can be better detected and in particular provide a better signal-to-noise ratio. A further advantage of a high modulation frequency component is that the time resolution of the relative phase measurement is improved. However, if the inverse frequency or period of the modulation is less than the travel time of the acoustic signal from its generation to its detection, then the relative phase can only be determined modulo 360°. In order to resolve this ambiguity in the relative phase, it is therefore preferable to also provide for a lower modulation frequency component, as will be explained below in more detail with reference to a specific embodiment.

In a preferred embodiment, the higher modulation frequency component is selected from a range of 50 kHz to 10 MHz, preferably of 100 kHz to 3 MHz, and the lower modulation frequency component is selected from a range of 1 kHz to 2 MHz, preferably of 10 kHz to 200 kHz.

Preferably, the method further comprises a step of adjusting the one or more modulation frequency components depending on the distance between the target region of the energy deposition and the detection apparatus. Choosing the frequency to match the distance can be inter alia done based on two considerations. The first consideration is that high frequency ultrasonic signals, although typically preferable with regard to their signal-to-noise ratio and the time resolution of the measurement, will be prone to a higher damping upon travel through the tissue. Accordingly, for a longer distance between the target region of the energy deposition and the detection apparatus, lower modulation frequencies may be chosen than for shorter distances. A second consideration has to do with ambiguity in the relative phase occurring at too high frequencies, as explained above. Accordingly, it is preferable if the modulation frequency components are not fixed but can be chosen based on the respective application and circumstances.

Preferably, the inverse of a first frequency component among said one or more modulation frequency components is shorter than the distance between the target region of the energy deposition and the detection apparatus, divided by the ultrasonic speed in said absorptive medium.

In addition, or alternatively, the inverse of a second frequency component among said one or more modulation frequency components is longer than the distance between the target region of the energy deposition and the detection apparatus, divided by the ultrasonic speed in said absorptive medium. This second frequency component would be low enough to resolve the ambiguity in the relative phase occurring for the aforementioned first frequency component.

Instead of using low modulation frequency components for resolving ambiguities in the relative phase, in one embodiment said intensity modulated ion beam comprises a timing feature that it time-related, in particular but not necessarily, synchronized with at least one of said one or more modulation frequency components, and which allows for a time-of-flight detection in a corresponding acoustic signal caused by said timing feature. In other words, while the present invention is generally based on frequency information in the ion beam and in the acoustic signals rather than on pure time-of-flight measurements, the method of the invention can still be combined with a time-of-flight measurement. For this purpose, certain timing features can be provided in the modulated ion beams that carry over to the acoustic signals and can be detected in a time-of-flight analysis, to thereby allow for resolving the ambiguity in relative phase when otherwise high modulation frequencies are used.

In a preferred embodiment, the ion beam may comprise a sequence of intensity bursts modulated with said one or more modulation frequency components with intermittent blanking periods, or a sequence of wavelets having said one or more modulation frequency components. In this instance, the aforementioned timing feature can be defined by one or both of the start or end of said bursts or wavelets, which can be subjected to a time-of-flight analysis, making a lower modulation frequency component dispensable.

In a preferred embodiment, the at least one detection apparatus comprises one or more frequency filters or one or more lock-in amplifiers The frequency filters or lock-in amplifiers may be either analogue or digital components.

In a preferred embodiment, said information regarding the location of energy deposition is one of an information about the position along the axis of the ion beam where the energy deposition per unit volume is maximum, or a one-, two- or three-dimensional energy dose distribution.

Preferably, the step of deriving information regarding the location of the energy deposition comprises determining higher moments of the energy deposition based on an analysis of higher harmonics of the modulation frequency components in the detected acoustic signal. This is one example of employing the additional frequency information in the ion beam that is carried over to the corresponding acoustic signals.

In a preferred embodiment, said intensity modulation comprises one of, or a super-position of two or more of a binary intensity modulation, a sinusoidal intensity modulation, or a triangular intensity modulation.

Herein, the duty ratio of the binary intensity modulation is preferably more than 0.1%, preferably more than 1% and most preferably more than 10%.

In a further embodiment, said intensity modulation has a dominant frequency varying in time, or in other words, a chirp. Again, analyzing of such chirps signals allows for a more sophisticated re-construction of the energy dose distribution. If a chirped intensity modulation is employed, a digital filter or a digital lock-in amplifier is preferably used.

In a preferred embodiment, said at least one detection apparatus comprises an ultrasound transducer, wherein said ultrasound transducer is preferably also adapted to record ultrasonic images of the absorption medium, and/or wherein said at least one detection apparatus comprises a piezoelectric element, in particular a PZT or a PVDF element. Using the same ultrasonic transducers both for detecting the acoustic signals attributable to the time dependent energy deposition in the absorptive medium and for taking images, particularly medical images of the absorptive medium allows for efficiently and reliably correlating the location of energy deposition with a target area within the absorptive medium, such as a tumor to be irradiated. A particularly advantageous embodiment combines the determination of information regarding the location of energy deposition with targeted contrast-enhanced ultrasound imaging. An example for targeted contrast-enhanced ultrasound imaging employs molecularly-targeted ultrasound contrast agents for assessing biological processes at the molecular level. These molecular ultrasound contrast agents may be nano- or micro-sized particles that are targeted to specific molecular markers by adding binding ligands onto the surface of the particle, such as antibodies or small peptides that may recognize receptor proteins involved in various disease processes. In particular, it becomes possible to identify biologically (more) active tumor areas, and to ensure that the energy deposition or dose is precisely directed to these areas.

Particularly useful ultrasound contrast agents are so-called microbubbles, which are typically formed by gas-liquid emulsions consisting of a gaseous core surrounded by a shell. Preferred microbubbles have a diameter of 1 to 4 µm. Such microbubbles act as ultrasound contrast agents because the gaseous core of the microbubbles causes a high echogenic response that results in a high contrast to tissue background ratio in the ultrasound images. However, non-microbubble based contrast agents consisting of submicron or nano-sized particles may also be employed in various embodiments of the invention. These particles may consist of liquid or solid colloids that range in the size of 10 nm to 1000 nm. An overview of molecular ultrasound imaging and corresponding contrast agents is given in Nirupama Deshpande, Andrew Needles, and Jürgen K Widmann, "*Molecular Ultrasound Imaging: Current Status and Future Directions*", Clin Radiol. July 2010, 65(7): 567-581.

Using targeted contrast-enhanced ultrasound imaging is advantageous over currently discussed approaches in which biological information from PET images is used which is typically acquired long before the treatment and hence not necessarily representative of the situation at the time of treatment, and also not naturally co-registered with the patient.

While it is currently preferred to use the contrast-enhanced ultrasound imaging based on the same transducers as the transducers used for detecting the acoustic signals attributable to the energy deposition in the absorptive medium, a related embodiment can also be employed together with separate ultrasound transducers exclusively provided for medical imaging. In this case, it is preferable if these additional transducers are nevertheless in a known spatial relationship with regard to the detection apparatuses employed for detecting the acoustic signals attributable to the energy deposition in the absorptive medium. In many cases, the transducers for medical images will be designed for different, in particular higher detection frequencies than the transducers used for detecting the acoustic signal attributable to the time dependent energy deposition in the absorptive medium by the intensity modulated ion beam. For example, in some embodiments, the transducers for detecting the acoustic signal due to the modulated ion beam may be designed for detection in a range of 50 to 150 kHz, while the ultrasound transducers for medical images, in particular for imaging tumor tissue would be devised for higher frequencies of e.g. several MHz, so that the transducers employed could be of quite different design.

The detection apparatus may further comprise a detector for detecting γ-radiation indicative of the deposition of energy by the ion beam. The γ-radiation detector may be a scintillation detector or a solid state detector. Receipt of γ-radiation may serve as a zero-time based on which the time lag of the acoustic signal can be determined.

In a preferred embodiment, said at least one detection apparatus is located within a cone having its apex at the position along the ion beam axis where the energy deposition per unit volume is maximum, a rotation axis coinciding with the ion beam axis, and an aperture angle of 45° or less, preferably 25° or less and most preferably 12° or less. In particular, the detection apparatus may be located directly on the ion beam axis. Placing the detection apparatus on or close to the ion beam axis is particularly useful for measuring the location of the Bragg peak along the ion beam axis.

In a preferred embodiment, at least one of the one or more detection apparatuses is configured for insertion into a hollow organ, in particular into the gastro-intestinal tract, into the colon, into the rectum, into a blood vessel, into the urethra or into the bladder. Such a detection apparatus for internal use can be placed very closely to the target region, thereby keeping damping loss of the acoustic signal while propagating through the tissue to a minimum and enhancing the accuracy in the determination of the Bragg peak location.

In a preferred embodiment, said at least one detection apparatus comprises a plurality of detectors, in particular an array of detectors in a fixed spatial relationship, wherein the plurality of detectors preferably comprises a first group of detectors arranged in a first plane together with the ion beam axis, and a second group of detectors arranged in a second plane together with the ion beam axis, wherein said first and second planes are different from each other. This arrangement of detectors allows for a reconstruction of a three-dimensional energy dose distribution.

In a preferred embodiment, said location of energy deposition is a location with regard to a target area in said absorptive medium. Preferably, said target area is defined in a coordinate system of a medical image, and the step of deriving information regarding the location of energy deposition with regard to the target area comprises the steps of determining the location of energy deposition in a detection apparatus coordinate system, and co-registering the detection apparatus coordinate system with the medical image coordinate system.

Preferably, said step of co-registering the detection apparatus coordinate system with the medical image coordinate system is based on one or more of the following: a fixed spatial relationship between said one or more detection apparatuses and a medical imaging apparatus by which the medical image is taken or by which an auxiliary medical image is taken which may be aligned with the medical image, tracking the one or more detection apparatuses and said medical imaging apparatus or a navigation aid which is provided in or on said medium and is recognizable in the medical image using an optical and/or electromagnetic tracking device, or taking a medical image or an auxiliary medical image of the medium which also includes the one or more detection apparatuses.

Preferably, the method further comprises a step of determining whether the location of energy deposition with regard to said target area deviates from a treatment plan, and in case the deviation exceeds a predetermined threshold, deriving control or operating parameters such as to decrease the deviation, wherein the control or operating parameters preferably relate to the energy of the ion beam or positioning parameters for a treatment table on which a patient is placed. This way, the method allows for correcting the dose distribution in vivo, i.e. under/while providing radiation treatment.

The apparatus comprises an ion beam source capable of generating an intensity modulated ion beam, or a modulating unit for modulating the intensity of an ion beam, said intensity modulation comprising one or more modulation frequency components, at least one detection apparatus for detecting an acoustic signal attributable to a time-dependent energy deposition in said absorptive medium by said intensity modulated ion beam, said detection apparatus being preferably configured for extracting at least one modulation frequency component of the acoustic signal corresponding to a respective one of the one or more modulation frequency components of said intensity modulation, or a harmonic thereof, and an analyzing unit for deriving information regarding the location of the energy deposition based, at least in part, on a time lag between the timing of the intensity modulation and said acoustic signal.

In a particularly advantageous embodiment, the ion source may comprise a synchro-cyclotron emitting pulsed ion beams. In a synchro-cyclotron, the frequency of the driving RF electric field is varied to compensate for relativistic effects. Synchro-cyclotrons by their construction emit pulsed radiation, with an intensity within the pulse which is comparatively high and thereby has the capability of leading to comparatively strong acoustic signals. When employed in the present invention, the pulses outputted by the synchro-cyclotron may be further intensity modulated with one or more frequency components. Using synchro-cyclotrons, it may be sufficient to use a single modulation frequency, while the beginning and/or end of the individual pulses can be used as "timing features" in the sense explained above, which allows for a time-of-flight detection in a corresponding acoustic signal. In fact, a modulated output of a synchro-cyclotron can be regarded as an example of bursts modulated with modulation frequency components with intermittent blanking period, as referred to above.

In a preferred embodiment, the modulating unit comprises a chopper, or two or more choppers operating at different chopping frequencies. The chopper is preferably formed by an electrical or magnetic deflecting unit. The chopper may be located at an ion source, prior to acceleration, within the accelerator acting on the partly accelerated ion beam, or downstream of the accelerator acting on the fully accelerated ion beam.

SHORT DESCRIPTION OF THE FIGURES

FIG. 3a shows the waveform of an intensity-modulated ion beam.

FIGS. 3b/3c show the frequency components of the modulated ion beam of FIG. 3a.

DESCRIPTION OF THE PREFERRED EMBODIMENTS

For the purposes of promoting an understanding of the principles of the invention, reference will now be made to the preferred embodiments illustrated in the drawings and specific language will be used to describe the same. It will, nevertheless, be understood that no limitation of the scope of the invention is thereby intended, such alterations and further modifications in the illustrated device and such further applications of the principles of the invention as illustrated therein being contemplated as would normally occur now or in the future to one skilled in the art to which the invention relates.

Figure 2:
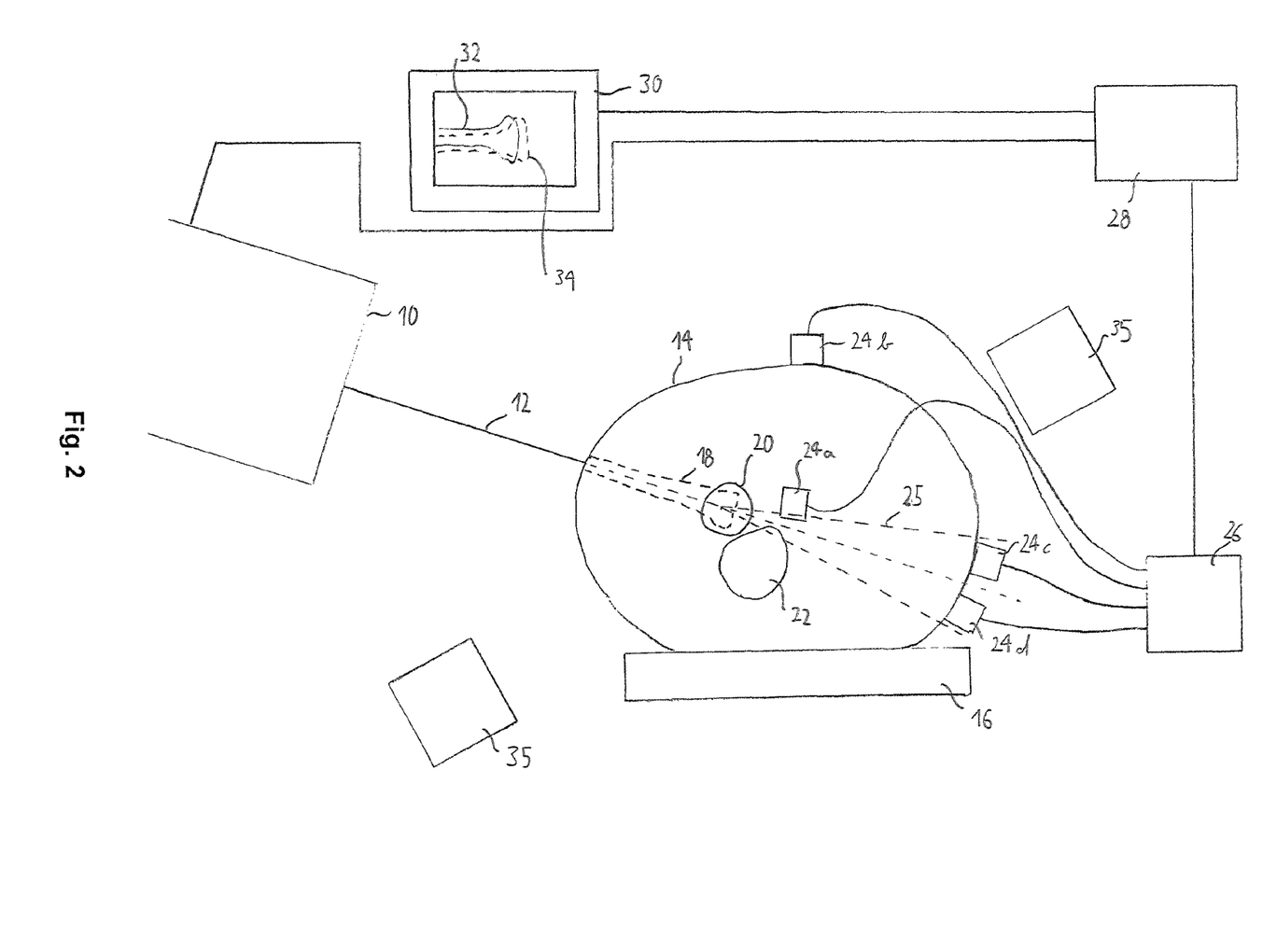
FIG. 2 is a schematic illustration of a radiation therapy system employing an apparatus for determining information regarding the location of energy deposition of an ion beam according to an embodiment of the invention.

FIG. 2 is a schematic view of a proton therapy apparatus comprising an apparatus for determining information regarding the location of energy deposition of a proton beam 12 in the tissue of a patient 14 undergoing radiation therapy.

In particular, FIG. 2 shows an exit region of a proton accelerator 10 emitting a proton beam 12. While in the description of the specific embodiment reference to a proton beam is made, the same disclosure would equally apply to any therapeutic type of ion beam, including helium, lithium, boron, carbon, nitrogen, oxygen, fluorine and neon ions.

As is further seen in FIG. 2, the proton beam 12 enters the body 14 (shown in a sectional view) of a patient placed on a treatment table 16. The treatment table 16 can be translationally and rotationally adjusted for placing the patient 14 with respect to the ion beam 12 so that the energy of the ion beam 12 will be deposited at a desired target region, e.g. at a tumor site indicated at reference sign 20. In FIG. 2, the region of energy deposition of the proton beam 12 is schematically indicated at reference sign 18.

The energy of the ion beam 12 is adjusted so that the end of the energy deposition region 18 coincides with the tumor location 20 (or a given location within the tumor 20). As explained in the introductory portion of the specification with reference to FIG. 1, the energy deposition increases with penetration depth and reaches its maximum at the so-called Bragg peak, close to the maximum penetration depth.

The energy of the proton beam 12 must be precisely adjusted so that the Bragg peak coincides with the location of the tumor 20 or with a certain voxel of the tumor that is intended to be treated according to the treatment plan. If the energy is too low, then part of the tumor will not be irradiated. If the energy is too high, then the Bragg peak would lie behind the tumor 20 (with respect to the propagation direction of the proton beam 12) and would affect healthy tissue or—even worse—an organ at risk indicated at 22 in FIG. 2. It is hence seen that when delivering the beam 12 to the tumor 20 it is not only necessary that the axis of the proton beam 12 is precisely adjusted such as to point to the tumor 20, but that the energy of the proton beam 12 is precisely adjusted, too.

Further four ultrasonic transducers 24a-24d are shown in FIG. 2. The ultrasonic transducer 24a is located in the colon (not shown) of the patient 14. The transducers 24b-24d are in contact with the skin of the patient 14. The transducers 24c and 24d are located within a cone 26 having its apex at the position along the axis of the ion beam 12 where the energy deposition per unit volume is maximum (i.e. at the Bragg peak location), a rotation axis coinciding with the ion beam 12 axis and an aperture angle of approximately 20°. While not shown, in a preferred embodiment a transducer would also be placed directly on the ion beam 12 axis.

The transducers 24a-24d are connected with an analyzer unit 26 comprising lock-in amplifiers (not shown). By use of the lock-in amplifiers, predetermined frequency components of an acoustic signal can be extracted and amplified to provide for a high signal-to-noise ratio.

The analyzing unit 26 is coupled with a computer 28. The computer 28 is further coupled with a modulation unit and/or a control unit (not shown) associated with the proton accelerator 10.

FIG. 2 schematically shows a display 30 on which a dose distribution 32 according to a treatment plan and the actual dose distribution 34 are schematically shown. Finally, a CT device 35 for proper patient placement is shown.

Figure 3:
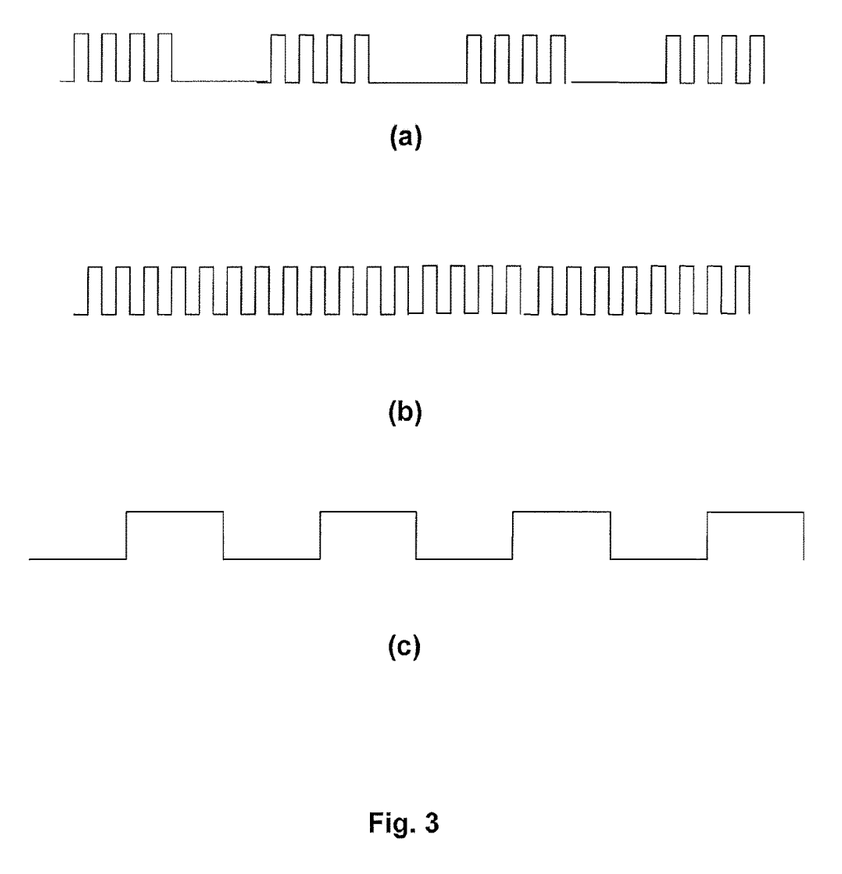
Figure 4:
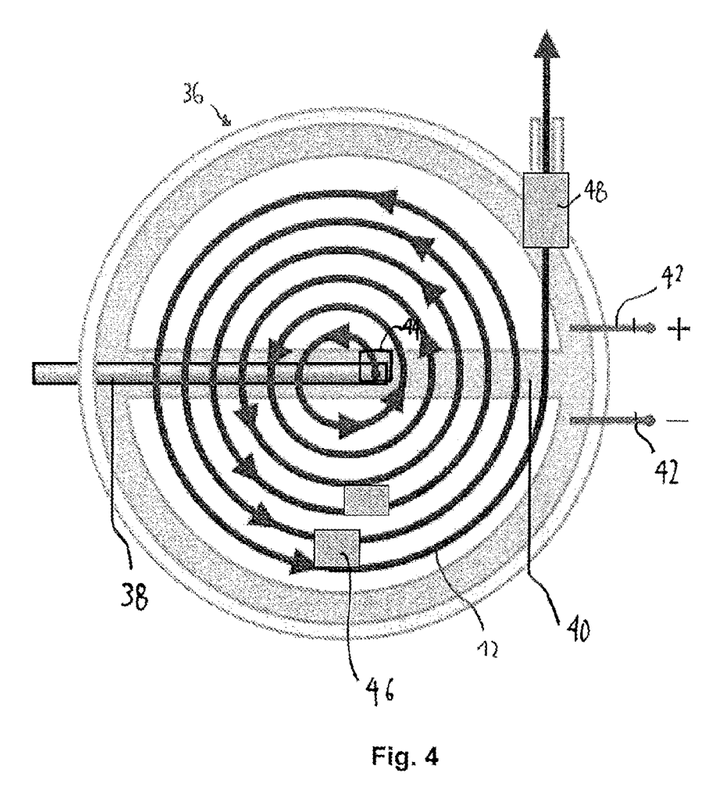
FIG. 4 is a schematic view of a cyclotron including choppers for modulating an ion beam intensity.
Figure 5:
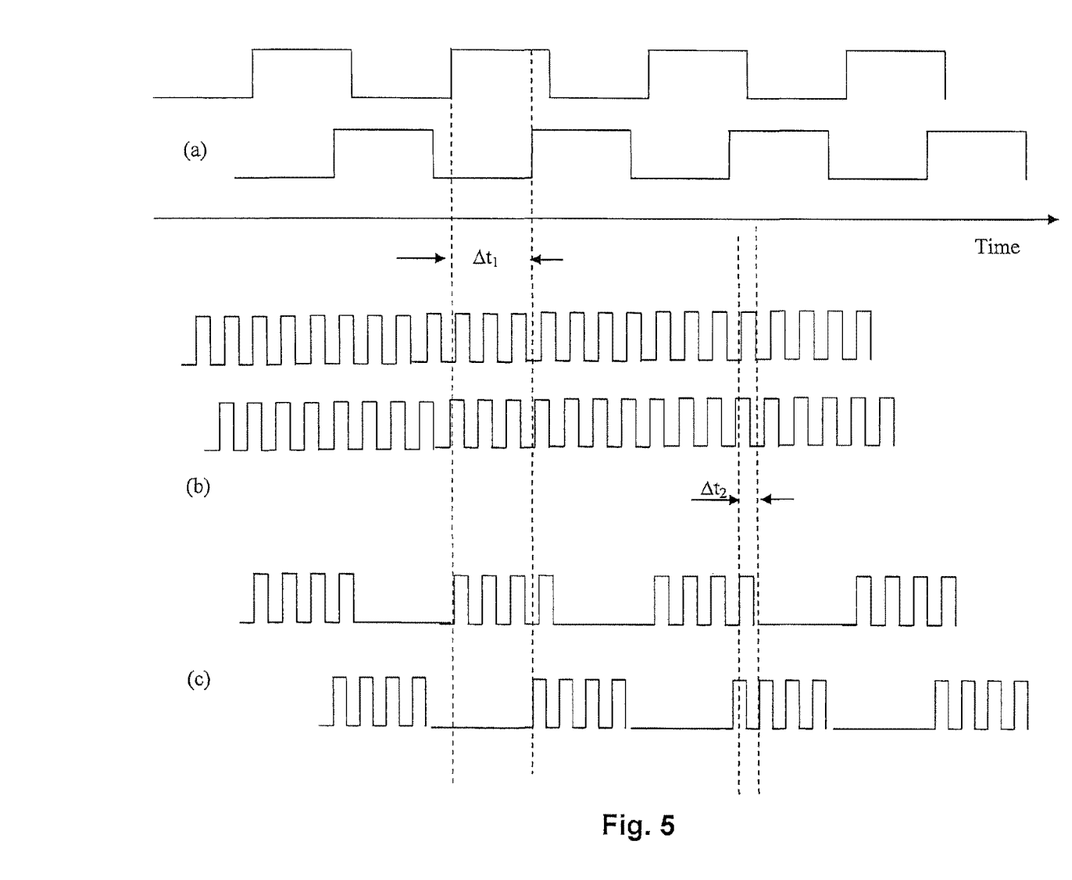
FIGS. 5a-5c show pairs of waveforms with a time lag to illustrate ambiguities in relative phase for higher frequencies.

Next, the operation of the treatment system of FIG. 2, and in particular of the apparatus for determining information regarding the location of energy deposition of the proton beam 12 in the tissue of patient 14 is described with further reference to FIGS. 3 to 5.

Different from ordinary proton therapy apparatuses, the proton beam 12 of the invention is intensity-modulated, wherein in the specific embodiment shown, the intensity modulation comprises two modulation frequency components, namely a first modulation frequency component which is a higher modulation frequency component and may for example be at 800 kHz, while the second modulation frequency component is a lower modulation frequency component of for example 200 kHz, i.e. a fourth of the first or higher modulation frequency component. A schematic time-intensity diagram of the ion beam 12 is shown in FIG. 3a.

FIG. 4 shows a schematic view of a cyclotron 36 which is part of the proton accelerator 10 and is adapted for generating said intensity-modulated proton beams. The cyclotron 36 of FIG. 4 comprises an ion source 38, an acceleration gap 40 and acceleration electrodes 42, in the usual manner. The spiraling ion beam is shown at reference sign 12 in FIG. 4 as before.

At the output of the ion source 38, a first chopper 44 is provided which chops the ion beam 12 prior to acceleration in the cyclotron 36 with the aforementioned first modulation frequency component, to thereby obtain a proton beam 12 that is intensity modulated according to the first modulation frequency component, as shown in FIG. 3b. The first chopper 44 is an example of the generic modulation unit referred to in the summary of the invention above.

A second chopper 46 is provided in the cyclotron 36 and chops the partially but not yet fully accelerated ion beam 12 with the second modulation frequency component. FIG. 3c shows the intensity modulation effected by the second chopper 46 if applied to a constant ion beam. However, since the ion beam 12 present at the second chopper 46 has already been intensity modulated by the first chopper 44, the resulting intensity-modulated beam of FIG. 3a is obtained, which comprises two modulation frequency components. In the present disclosure, a "modulation frequency component" may in particular refer to "main frequency components" or frequency components that have corresponding peaks in the corresponding Fourier spectrum of the beam.

Note that the location and the type of choppers 44, 46 are only exemplary, and that various modifications are possible. In particular, an alternative chopper could also be operated such that a single chopper would provide the intensity modulation comprising two or more frequency components. Also, other locations for the one or more choppers are possible. For example, in FIG. 4 a further chopper location 48 is shown, which is located downstream of the cyclotron 36, and hence chops the fully accelerated proton beam 12. Further, there are other possibilities to generate intensity modulated proton beams or ion beams in general, including a modulation of the ion source 38 or the like. One advantage of using choppers such as the first and second choppers 44, 46 is that they can be operated precisely and flexibly at high frequencies, and that they are very reliable, which is of prime importance in view of the fact that the intensity modulation plays a pivotal role in the dose monitoring and hence for the safety of the entire treatment. In particular, the first and second choppers 44, 46 may comprise a deflection unit in which the proton beam 12 is chopped by corresponding deflections of the proton beam 12. Since the beam 12 is constituted of charged particles, it can be deflected either by electric fields, magnetic fields or both.

Figure 6:
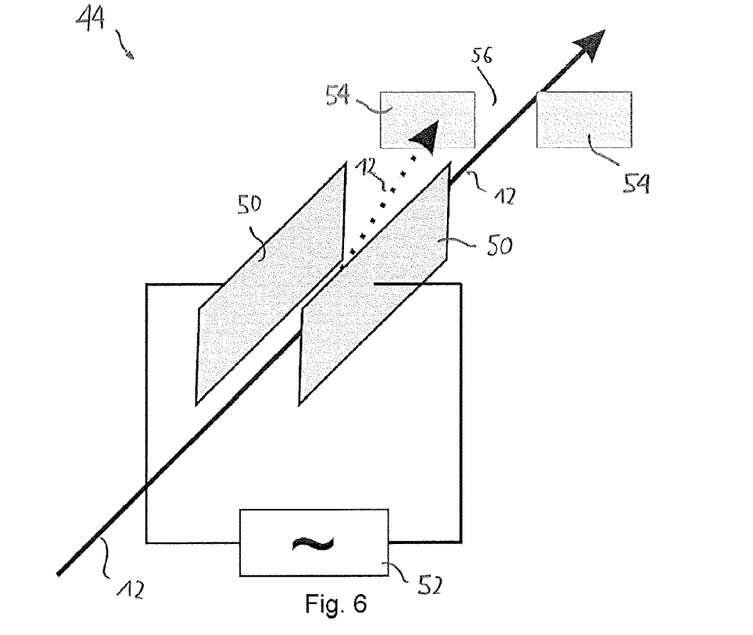
FIG. 6 is a schematic illustration of a chopper employing an electric deflection field.

FIG. 6 schematically shows an exemplary embodiment of the first chopper 44 of FIG. 4. As shown therein, the chopper 44 comprises a pair of deflection plates 50 connected to a high frequency, high voltage generator 52. Further, the chopper 44 comprises a screen 54 provided with a slit 56. If no voltage is applied between the deflection plates 50, the proton beam 12 passes through the space between the deflection plates 50 without deflection and further passes through the slit 56. If, however, a voltage is applied between the deflection plates 50, the proton beam 12 is deflected, as indicated by the dotted arrow in FIG. 6 and therefore fails to pass through the slit 56 but is blocked by the screen 54 instead. This way the proton beam 12 can be chopped according to the voltage applied to the deflection plates 50. In order to enhance the voltage applied to the deflection plates 50 such as to obtain sufficient deflection angles, especially for high energy proton beams, the high frequency, high voltage generator 52 may comprise a resonator structure that magnifies the voltage of a high frequency power supply by the quality factor of the resonator at the applied frequency.

Figure 7:
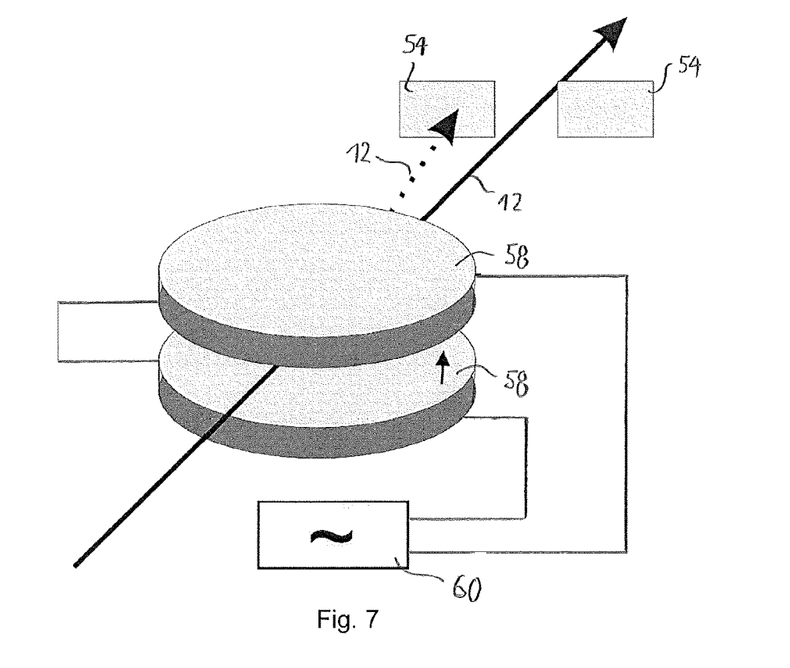
FIG. 7 is a schematic illustration of a chopper employing a magnetic deflection field.

Instead of deflecting the ion beam 12 by means of an electric field between deflector plates 50, it is likewise possible to deflect the proton beam 12 using a magnetic field, as is schematically shown in FIG. 7. In the chopper 44 of FIG. 7, a pair of coils 58 is used instead of the deflection plates 50 of FIG. 6. Further, instead of a high frequency, high voltage generator, a high frequency current generator 60 is employed. Again, a high frequency resonator structure (not shown) can be used to increase the obtainable currents. The coils 58 may be air-core coils or iron filled coils. The coils 58 may in particular be superconducting coils. Since switching high magnetic fields at high frequencies is rather demanding, the chopper 44 of FIG. 6 employing electric fields generated by the deflector plates 50 is currently preferred.

While in FIGS. 6 and 7 exemplary embodiments of the first chopper 44 have been shown, the same structure can also be used for the second chopper 46 of FIG. 4.

Figure 8:
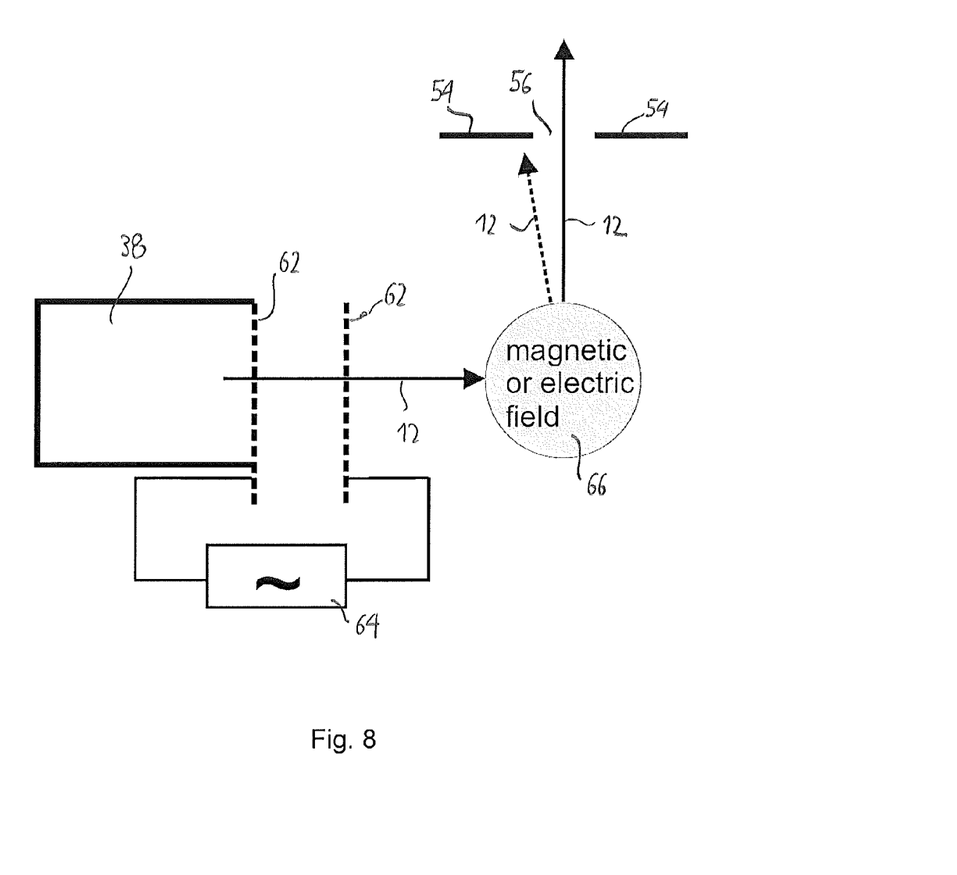
FIG. 8 is a schematic view of an ion beam intensity modulator.

FIG. 8 shows a yet further apparatus of modulating the intensity of the ion beam 12. In FIG. 8, an ion source 38 and a pair of extraction or acceleration electrodes 62 are shown. A voltage between the extraction/acceleration electrodes 62 is generated by a high frequency, high voltage generator 64. By switching the voltage between the extraction/acceleration electrodes 62 on and off, the proton beam 12 can be effectively switched on and off as well.

Instead of switching the voltage between the electrodes 62 on and off, it is also possible to only modulate the voltage, thereby modulating the energy of the proton beam 12. When passing a magnetic or electric field, which is schematically indicated at reference sign 66, the proton beam 12 will be deflected with an angle depending on the beam energy. This can again be used to allow the proton beam 12 to selectively pass through a slit 56 in a screen 54 or to be blocked depending on the beam energy, or, in other words, on the acceleration voltage applied.

As mentioned in the introduction of the present specification, the energy deposition of an ion bunch in the tissue gives rise to a local temperature increase and a corresponding pressure spike, which in turn leads to an ultrasound signal. Since in the embodiment of the invention, the ion beam is intensity modulated with one or more modulation frequency components, these modulation frequency components will be present in the generated ultrasonic signals as well. And since the modulation frequency is known, the expected modulation frequency components of the acoustic signal can be extracted by the detection apparatus to thereby allow for a very high signal-to-noise ratio, such that even weak ultrasonic signals can be reliably detected. In the embodiment shown in FIG. 2, this is achieved by using lock-in-amplifiers (not shown) included in the analyzer unit 26. Alternatively, the expected modulation frequency component of the acoustic signal can also be extracted using suitable narrow band filters or the like. In this case, too, the signal-to-noise ratio can be increased, and even weak acoustic signals can be reliably detected.

The first or higher modulation frequency component may be chosen such that the strength of the detected acoustic signal is optimum. It is seen that higher frequencies tend to allow for a better signal strength and a better signal-to-noise ratio than lower frequencies. However, a higher frequency of the ultrasonic signal leads to a higher damping of the acoustic signal upon its travel through the tissue. If the detector is located very close to the target region (tumor 20), such as the transducer 24a of FIG. 2 which is located in the colon right next to the tumor 20, higher modulation frequency components of for example one or several Megahertz may be desirable. If the distance is larger, as is for example the case for the transducers 24b-24d, the first modulation frequency component may be chosen to be somewhat lower. In the embodiment shown in FIG. 2, both the modulation frequency components of the proton beam 12 and the detection frequencies of the analyzer unit 26 can therefore be adjusted under the control of the computer 28 for optimum detection results.

Since the ultrasonic speed in the tissue is limited, there will be a time lag between the interaction of the ion beam 12 with the tissue and the corresponding part of the acoustic signal received at the transducers 24a-24d which time lag is proportional to the respective distance. From this time lag and the related distance information, the information regarding the location of energy deposition can be derived, which is also done by the computer 28. The point in time of the interaction of the ion beam 12 with the tissue can be determined in various ways. One way is to derive it from the time control of the proton accelerator 10 itself, or from the time control of the modulators employed for generating the intensity modulated ion beam, such as the choppers 44, 46 described above. Alternatively, the point in time of the interaction of the ion beam 12 with the tissue can be detected via γ-radiation caused thereby, using suitable γ-detectors such as scintillation detectors or solid state γ-detectors (not shown). Since the gamma rays propagate with the speed of light, unlike the acoustic signal they are not subject to any significant time lag. In a preferred embodiment, the γ-detectors are integrated with the transducers 24a-24d, which allows for a particularly easy way of determining the time lag between the interaction of the ion beam 12 with the tissue and the corresponding part of the acoustic signal received at the transducers 24a-24d.

In the described embodiment, the "time lag" can be regarded as a relative phase between the intensity modulation of the proton beam 12 and the acoustic signal which likewise reflects the modulation of the proton beam intensity. However, if the distance between the target region of energy deposition, (i.e. the tumor 20) and the transducers 24a-24d exceeds the inverse of the modulation frequency component divided by the ultrasonic speed in the tissue, then the relative phase will be more than 360°. However, the relative phase shift between the intensity-modulated proton beam and the oscillatory acoustic signal can generally only be determined modulo 360°, so that the total time lag cannot be easily determined. This would at first sight speak in favor of lower modulation frequency components. However, the inventors have noticed that higher modulation frequency components, for example in the order of a Megahertz, are favorable both with regard to the achievable signal-to-noise ratio and to the time resolution and hence to the precision of the time lag measurement. Accordingly, in a preferred embodiment, the ambiguity in relative phase up to multiples of 360° is preferably accepted in favor of higher modulation frequency components, and the ambiguity is e.g. resolved by a second, lower modulation frequency component, where the time lags that may occur will always be lower than the inverse frequency.

This situation is illustrated with reference to FIGS. 5a-5c. FIG. 5a shows two lower frequency signals where the possible time lag between the two signals is less than the inverse frequency of the signal. Accordingly, the phase shift $\Delta t_1$ between the two signals can be unambiguously determined because it can be assumed that it will always be less than 360°. FIG. 5b shows the same time lag for two higher frequency signals where the apparent time lag $\Delta t_2$ actually ignores three inverse higher frequencies and can therefore not be unambiguously determined.

FIG. 5c finally shows two intensity-modulated signals each having two modulation frequency components, at the first and at the second frequency, as is the case for the intensity-modulated ion beam of the instant embodiment shown in FIG. 3a. Clearly, the second (lower) frequency component of the signal can be used to resolve the ambiguity of the phase of the first (higher) frequency component of the modulation. At the same time, the advantages of the first modulation frequency component with regard to signal-to-noise ratio and time resolution can be fully exploited.

In summary, the computer 28, together with the analyzer unit 26, can determine a distance between the location of energy deposition and each of the transducers 24a-24c based on the time lag between the proton beam 12 modulation and the acoustic signal reflecting this modulation. In the simplest case, this can be used to determine the location of the Bragg peak along the axis of the proton beam 12. This can be best done with a transducer (not shown) that is located directly on the proton beam axis, but can be also determined with transducers 24c and 24d located within the cone 25 or, in other words, close to the proton beam 12 axis. This is actually a very important application of the invention because it allows to appropriately choose the energy of the proton beam, which can currently be regarded as one of the most critical aspects of proton beam therapy.

However, using a plurality of transducers located at different locations, as indicated by transducers 24a-24c, a two- or even three-dimensional energy dose distribution can be determined. A more detailed reconstruction of the three-dimensional energy dose distribution can further be derived based on determining higher moments of the energy position based on an analysis of higher harmonics of the modulation frequency components in the detected acoustic signal. This is an example of how the "frequency information" introduced to the intensity modulated proton beam 12 can be employed for dose reconstruction purposes.

In practical applications, the energy is to be deposited within a target area that is defined in the coordinate system of a medical image taken prior to the radiation treatment and stored in the computer 38 according to a so-called treatment plan. However, with the procedure described so far, the location of the energy that is actually deposited is only determined in relation to the detection apparatus (e.g. the transducers 24a-24d) or, in other words, with regard to a "detection apparatus coordinate system". Accordingly, in order to derive the information regarding the location of energy deposition with regard to the target area, it will typically be necessary to determine the location of the energy deposition in a detection apparatus coordinate system and to then co-register the detection apparatus coordinate system with a medical image coordinate system. This co-registering of the detection apparatus coordinate system with the medical image coordinate system can for example be based on a fixed spatial relationship between the one or more detection apparatuses 24a-24d and a medical imaging apparatus by which the medical image is taken, or by which an auxiliary medical image is taken which may be aligned with the medical image. In the embodiment shown in FIG. 2, the transducers 24a-24d are not only capable of detecting the acoustic signals caused by the proton beam 12, but can also be used to record ordinary ultrasound images of the patient 14. Such ordinary ultrasound image is an example of an "auxiliary medical image" which can then be aligned with the medical image on which a treatment plan is based and which is stored in the computer 28.

Preferably, molecularly-targeted ultrasound contrast agents such as microbubble based contrast agents are employed which allow for identifying the biologically (more) active tumor areas. This allows for identifying these areas as well as confirming that the dose is delivered precisely at these preferred locations at the time of treatment.

Based on this co-registering, the treatment plan 32 and the true dose distribution 34 detected using the apparatus of the invention can be compared, as is shown schematically under reference signs 32 and 34 in FIG. 2. As indicated in FIG. 2, the dose distribution 32 according to the treatment plan and the actual dose distribution 34 do in fact deviate, both with regard to a lateral shift (which can be compensated by moving the treatment table 16) but also with regard to the penetration depth, which in the example of FIG. 2 is too high, and which calls for a decrease in the energy of the proton beam 12 under the control of the computer 28.

In the present embodiment, the computer 28 is adapted to constantly determine whether the location of the energy deposition with regard to the target area deviates from the treatment plan, and in case a deviation exceeds a predetermined threshold, to derive control or operating parameters such as to decrease the deviation, in particular the energy of the proton beam or the positioning parameters of the treatment table 16 on which the patient 14 is placed.

The possibility of using the same transducers 24a-24d both for determining the location of energy deposition and for taking medical images gives rise to a particularly powerful and convenient operation. However, the invention is not limited to this. In particular, there are other possible ways of co-registering the detection apparatus coordinate system with the medical image coordinate system. For example, it would be possible to track the positions of the transducers 24a-24c together with the CT apparatus 35, or together with a navigation aid provided in or on the patient 14 using an optical and/or electromagnetic tracking device. In addition, co-registering can also be achieved by taking a medical image or an auxiliary medical image, for example using the CT device 35, which also includes the transducers 24a-24c.

In a further preferred embodiment, the ion beam source may comprise a laser-accelerated ion beam source based on a target normal sheath acceleration for emitting pulsed ion beams, wherein the pulse intensity is preferably $10^8$ ions/ns or more. This novel ion beam source can be used with any of the previous embodiments if applicable. However, in view of the very high intensity of the pulses, the corresponding acoustic signals are so strong that the signal-to-noise ratio is acceptable even without using frequency selective filtering or lock-in amplification. In other words, with this particular ion beam source, even ordinary time-of-flight measurements are expected to give appropriate results.

Such compact, laser based acceleration schemes have been discussed for example in Malka et al. 2007, *"Principles and applications of compact laser-plasma accelerators"*, *Nature physics* 4 (2008) 447 or in Daido et al. 2012, *Rep. Prog. Phys.* 75 (2012) 056401, included herein by reference.

Note that the generation of laser-accelerated ions leads to a strong electromagnetic pulse, or in other words, a transient electromagnetic disturbance that has a tendency to disturb or even damage electronic equipment. However, since the detection of the corresponding acoustic signal is delayed according to the travel time, the detection can occur at a time where the electromagnetic pulse is over, so that the detection will generally not be disturbed thereby. Accordingly, it turns out that any difficulties typically encountered with electromagnetic pulses can be largely avoided in practical implementations.

The examples described above and the drawings merely serve to illustrate the invention and its advantages over the prior art, and should not be understood as a limitation in any sense. The scope of the invention is solely determined by the appended set of claims.

While in the preceding description, particular emphasize was taken on energy deposition of an ion beam in the tissue of a patient undergoing radiation therapy, the method and apparatus of the invention is by no means limited to this. For example, the invention is also applicable for assessing an ion beam range and shape in a phantom, such as in a water tank or other tissue-equivalent materials, as could e.g. be used for pre-treatment verification of a treatment plan, consistency check of the ion beam parameters and the like.

Further applications of the invention are entirely unrelated to medical or biological applications. For example, focused ion beams can be used for implantation purpose for locally modifying materials, e.g. in the semiconductor technology, or other material science applications.

The method and apparatus of the invention could also be used in focused ion beam devices enabling the processing of materials in a micrometer or sub-micrometer range, where likewise the determination of information regarding the location of energy deposition would be of interest. For these purposes too, an intensity modulated ion beam could be used, and a detection as set forth above could be employed. This application would not be limited to determining the insertion depth only, but could also be used to determine the position of the beam in the medium in two or three dimensions. In some of these applications, higher modulation frequencies up to 100 MHz could be of interest in order to obtain a spatial resolution of less than 1 μm.

REFERENCE SIGNS 10 proton accelerator
12 proton beam
14 patient undergoing radiation therapy
16 treatment table
18 energy deposition region
20 tumor
22 organ at risk
24a-24d ultrasonic transducers
25 cone
26 analyzer unit
28 computer
30 display
32 dose distribution according to treatment plan
34 actual dose distribution
35 CT device
36 cyclotron
38 ion source
40 acceleration gap
42 acceleration electrodes
44 first chopper
46 second chopper
48 alternative chopper location
50 deflection plates
52 high frequency, high voltage generator
54 screen
56 slit
58 pair of coils
60 high frequency current generator
62 extraction/acceleration electrodes
64 high frequency, high voltage generator
66 magnetic or electric field

The invention claimed is:

1. A method of determining information regarding the location of energy deposition of an ion beam the tissue of a patient undergoing radiation therapy, comprising the following steps:
   generating an intensity modulated ion beam, wherein the intensity modulation comprises one or more modulation frequency components,
   detecting an acoustic signal attributable to the time dependent energy deposition in said absorptive medium by said intensity modulated ion beam using at least one detection apparatus, said detection apparatus being configured for extracting at least one modulation frequency component of the acoustic signal corresponding to a respective one of the one or more modulation frequency components of said intensity modulation, or a harmonic thereof, and
   deriving information regarding the location of the energy deposition based, at least in part, on a time lag between the timing of the intensity modulation of said ion beam and said acoustic signal.

2. The method of claim 1, wherein the time lag is determined by determining a relative phase between the intensity modulation of the ion beam and the acoustic signal.

3. The method of claim 1, wherein the intensity modulation comprises one or more modulation frequency components in a range of 1 kHz to 10 MHz.

4. The method of claim 1, wherein said intensity modulation comprises a higher modulation frequency component and a lower modulation frequency component, wherein the frequency of the higher modulation frequency component exceeds the frequency of the lower modulation frequency component by a factor of at least 2.

5. The method of claim 4, wherein said higher modulation frequency component is selected from a range of 50 kHz to 10 MHz and
   wherein the lower modulation frequency component is selected from a range of 1 kHz to 2 MHz.

6. The method of claim 1, further comprising a step of adjusting the one or more modulation frequency components depending on the distance between the target region of the energy deposition and the detection apparatus.

7. The method of claim 1, wherein the inverse of a first frequency component among said one or more modulation frequency components is shorter than the distance between the target region of the energy deposition and the detection apparatus divided by the ultrasonic speed in said absorptive medium.

8. The method of claim 1, wherein the inverse of a second frequency component among said one or more modulation frequency components is longer than the distance between the target region of the energy deposition and the detection apparatus divided by the ultrasonic speed in said absorptive medium.

9. The method of claim 1, wherein said intensity modulated ion beam comprises a timing feature that is time-related with at least one of said one or more modulation frequency components, and which allows for a time-of-flight detection in a corresponding acoustic signal caused by said timing feature.

10. The method of claim 1, wherein said ion beam comprises one of a sequence of intensity bursts modulated with said one or more modulation frequency components with intermittent blanking periods, and a sequence of wavelets having said one or more modulation frequency components.

11. The method of claim 9, wherein the timing feature is defined by one or both of the start or end of said bursts or wavelets.

12. The method of claim 1, wherein the at least one detection apparatus comprises one or more frequency filters or one or more lock-in amplifiers.

13. The method of claim 1, wherein said information regarding the location of energy deposition is one of
   an information about the position along the axis of the ion beam where the energy deposition per unit volume is maximum, or
   a one-, two- or three-dimensional energy dose distribution.

14. The method of claim 1, wherein the step of deriving information regarding the location of the energy deposition comprises determining higher moments of the energy deposition based on an analysis of higher harmonics of the modulation frequency components in the detected acoustic signal.

15. The method of claim 1, wherein said intensity modulation comprises one of, or a super-position of two or more of
   a binary intensity modulation,
   a sinusoidal intensity modulation, or
   a triangular intensity modulation.

16. The method of claim 15, wherein the duty ratio of the binary intensity modulation is more than 1%.

17. The method of one the preceding claim 1, wherein said intensity modulation has a dominant frequency varying in time.

18. The method of claim 1, wherein said at least one detection apparatus comprises one of an ultrasound transducer and,
   a piezo-electric element.

19. The method of one the preceding claim 1, wherein said at least one detection apparatus is located within a cone having
   an apex at the position along the ion beam axis where the energy deposition per unit volume is maximum,
   a rotation axis coinciding with the ion beam axis, and
   an aperture angle of 25° or less.

20. The method of claim 1, wherein at least one of the one or more detection apparatuses is configured for insertion into one of the gastro-intestinal tract, the colon, the rectum, a blood vessel, the urethra, and the bladder.

21. The method of claim 1, wherein said at least one detection apparatus comprises a plurality of detectors in a fixed spatial relationship,
   wherein the plurality of detectors preferably comprises a first group of detectors arranged in a first plane together with the ion beam axis, and a second group of detectors arranged in a second plane together with the ion beam axis, wherein said first and second planes are different from each other.

22. The method of claim 1, wherein said location of energy deposition is a location with regard to a target area in said absorptive medium.

23. The method of claim 22, wherein said target area is defined in a coordinate system of a medical image, and
   wherein the step of deriving information regarding the location of energy deposition with regard to the target area comprises the steps of
   determining the location of energy deposition in a detection apparatus coordinate system, and
   co-registering the detection apparatus coordinate system with the medical image coordinate system.

24. The method of claim 23, wherein said step of co-registering the detection apparatus coordinate system with the medical image coordinate system is based on one or more of the following:
   a fixed spatial relationship between said one or more detection apparatuses and a medical imaging apparatus by which the medical image is taken or by which an auxiliary medical image is taken which may be aligned with the medical image,
   tracking the one or more detection apparatuses and
     said medical imaging apparatus or
     a navigation aid which is provided in or on said medium and is recognizable in the medical image,
     using an optical and/or electromagnetic tracking device,
   taking a medical image or an auxiliary medical image of said absorptive medium which also includes the one or more detection apparatuses.

25. The method of claim 22, further comprising a step of determining whether the location of energy deposition with regard to said target area deviates from a treatment plan, and in case the deviation exceeds a predetermined threshold, deriving control or operating parameters such as to decrease the deviation, wherein the control or operating parameters relate to one of the energy of the ion beam and positioning parameters for a treatment table on which a patient is placed.

* * * * *

UNITED STATES PATENT AND TRADEMARK OFFICE
CERTIFICATE OF CORRECTION

PATENT NO. : 10,441,817 B2
APPLICATION NO. : 15/327056
DATED : October 15, 2019
INVENTOR(S) : Günther Dollinger et al.

Page 1 of 1

It is certified that error appears in the above-identified patent and that said Letters Patent is hereby corrected as shown below:

In the Claims

In Column 16, Line 3:
Replace "beam the"
With --beam in the--

In Column 17, Line 28:
Delete "one the preceding"

In Column 17, Line 35:
Delete "one the preceding"

Signed and Sealed this
Seventh Day of January, 2020

Andrei Iancu
*Director of the United States Patent and Trademark Office*